United States Patent
Rajab (10) Patent No.: US 10,013,811 B2
(45) Date of Patent: Jul. 3, 2018

(54) HYPERSPECTRAL IMAGE VISUALIZATION IN PATIENTS WITH MEDICAL CONDITIONS

(71) Applicant: UMM AL-QURA UNIVERSITY, Makkah (SA)

(72) Inventor: Maher I Rajab, Makkah (SA)

(73) Assignee: Umm-Al-Qura University, Makkah (SA)

(*) Notice: Subject to any disclaimer, the term of this patent is extended or adjusted under 35 U.S.C. 154(b) by 0 days.

(21) Appl. No.: 15/181,209

(22) Filed: Jun. 13, 2016

(65) Prior Publication Data

US 2017/0354358 A1  Dec. 14, 2017

(51) Int. Cl.
*G06T 19/20* (2011.01)
*G06T 7/90* (2017.01)
*A61B 5/1455* (2006.01)
*A61B 5/00* (2006.01)
*G06T 7/00* (2017.01)

(52) U.S. Cl.
CPC .......... *G06T 19/20* (2013.01); *A61B 5/14551* (2013.01); *A61B 5/444* (2013.01); *A61B 5/445* (2013.01); *G06T 7/0012* (2013.01); *G06T 7/90* (2017.01); *G06T 2200/04* (2013.01); *G06T 2207/30096* (2013.01); *G06T 2219/2012* (2013.01)

(58) Field of Classification Search
None
See application file for complete search history.

(56) References Cited

U.S. PATENT DOCUMENTS

| | | | |
|---|---|---|---|
| 8,644,911 B1* | 2/2014 | Panasyuk | A61B 5/0075 600/473 |
| 2004/0141213 A1* | 7/2004 | Kleiman | H04N 1/484 358/474 |
| 2005/0023356 A1* | 2/2005 | Wiklof | G06K 7/10564 235/462.42 |
| 2006/0247514 A1* | 11/2006 | Panasyuk | A61B 5/0059 600/410 |
| 2014/0191113 A1* | 7/2014 | Atwater | H01L 27/14621 250/208.1 |
| 2015/0044098 A1* | 2/2015 | Smart | A61B 5/0013 422/82.05 |

OTHER PUBLICATIONS

Lu, Guolan, et al. "Spectral-spatial classification for noninvasive cancer detection using hyperspectral imaging." Journal of biomedical optics 19.10 (2014): 106004-106004.*
Lu, Guolan, et al. "Estimation of tissue optical parameters with hyperspectral imaging and spectral unmixing." Medical Imaging 2015: Biomedical Applications in Molecular, Structural, and Functional Imaging. vol. 9417. International Society for Optics and Photonics, 2015.*

* cited by examiner

Primary Examiner — Daniel Hajnik
(74) Attorney, Agent, or Firm — Geeta Kadambi; Ridhdi IP LLC (57) ABSTRACT

The present application discloses a novel algorithm to convert medical hyperspectral images (MHSI) into RGB (RedBlueGreen) images in different medical conditions by making use of the three spectral bands (Red, Green and Blue) of the MHSI and mapping them into Red, Green and Blue components for visualization of hyperspectral images.

8 Claims, 5 Drawing Sheets

Figure 4D
RGB Color image

Figure 4C
MHSI slice: Red band

Figure 4B
MHSI slice: Green band

Figure 4A
MHSI slice: Blue band

HYPERSPECTRAL IMAGE VISUALIZATION IN PATIENTS WITH MEDICAL CONDITIONS

FIELD OF TECHNOLOGY

The disclosure generally relates to visualization of spectral images produced from imaging devices in patients with medical conditions. In particular, the invention is directed to visualization of medical hyperspectral images produced from hyperspectral and multispectral imaging in patients with diabetic foot ulcers.

BACKGROUND

It has been estimated that around 26 million people in US suffer from diabetes in 2010 and the number will significantly increase by 2030. People suffering from diabetes have certain other complications related to heart disease and stroke, hypertension, blindness and other eye problems, kidney disease, nervous system disorder and lower-limb amputations. People 40 years or older with diabetes have reported impaired sensation in their feet and majority of them end up with amputation (1). Thus, diabetic foot ulcer is one of the common complications found among people suffering from diabetes. It occurs as a result of various factors, such as mechanical changes in confirmation of the bony architecture of the foot, peripheral neuropathy and atherosclerotic peripheral arterial disease which are common conditions in diabetic population. (2).

The problem is so severe that a number of special clinics have open up which particularly take care of foot ulcers in patients with diabetes. The clinic's decision of preserving the tissue and continuing medical management without surgical detriment is a critical one. This decision which predicts the clinic outcome of these patients depends on the physical clinical exam as well as the degree of the vascularity and the level of the oxygenation of the tissue within the ulcers and its surroundings.

Diabetic patients need at least yearly diagnosis of their feet even if they have no initial signs of foot ulcers. If they develop some signs they are first examined through general clinical examination followed by other techniques present such as-ankle brachial index (ABI), transcutaneous oxygen measurements (TCPO2), pulse volume recordings and laser droppler flowmetry among others. In recent years imaging spectroscopy known as hyperspectral imaging (HIS) have emerged in different fields including medicine and is thus called medical hyperspectral imaging (MHSI). MHSI shows image of the area/biological tissue under investigation by calculating the oxygen delivery and oxygen extraction of each pixel in the image collected. Thus, it has some important clinical advantages by detecting the levels of oxygenation with the effected tissue and its surroundings. However, with the current visualization methods the images produced do not give a clear, easy to analyze and informative image for the evaluation of the level of oxygenation and de-oxygenation to predict the severity of the disease.

The MHSI technology is used with full 2D image hyperspectral cameras to provide saturation maps of a large surface or with line or point probes to provide localized information of the biological tissue under investigation. The MHSI technology enables to determine blood oxygen saturation and carbon monoxide saturation from the reflected spectrum of the tissue. A spectrum is build up by measuring the intensity of light reflected from the biological tissue at many different visible wavelengths and thus show the response of biological tissue as a function of wavelength. However, the image spectrum obtained is difficult to analyze, require highly trained staff, high-tech computers and monitors and thus is sometimes poor in predicting the severity of the medical condition or the extent of damage in a particular medical condition.

Thus, high quality imaging and its visualization to determine oxygen saturation levels and mapping is one of the key steps for useful early and non-invasive diagnosis of medical conditions and more specifically early or routine diagnosis of diabetic foot ulcers.

SUMMARY

The invention discloses a novel visualization method of hyper spectral images (HIS) (HSI as disclosed in the present application may also include multispectral images) in patients with medical conditions. More specifically, the present invention relates to a novel visualization method of medical HSI (MHSI) in patients with medical conditions. In most conditions, the present invention relates to a novel visualization method of MHSI in patients with diabetic foot ulcers.

In one embodiment, the visualization method as disclosed converts a MHSI to a RGB image in patients with medical conditions. In another embodiment, the visualization method as disclosed converts the MHSI images to RGB images in patients with diabetes. In most embodiments, the visualization method as disclosed converts the MHSI images to RGB images in patients with diabetic foot ulcers.

In one embodiment, the visualization method as disclosed in the present application is via converting the MHSI to the RGB images in patients with medical conditions through a novel algorithm as disclosed in the present application. In another embodiment, the visualization method as disclosed in the present application is via converting the MHSI to the RGB images in patients with diabetes through a novel algorithm as disclosed in the present application. In most embodiments, the visualization method as disclosed in the present application is via converting the MHSI to the RGB images in patients with diabetic foot ulcers through a novel algorithm as disclosed in the present application.

In one embodiment, the disclosed algorithm utilizes the spectrum from MHSI to determine accurate oxygenation level, with an error of less than 0.1% to 0.5%. In another embodiment, the disclosed algorithm utilizes the spectrum from MHSI to determine accurate oxygenation level, with an error of less than 0.2%.

In one embodiment, the visualization method as disclosed in the present application helps to visualize the regions of ulceration. In another embodiment, the visualization method as disclosed in the present application helps to visualize the regions of tumor. In one embodiment, the visualization method as disclosed in the present application helps in mapping the regions of oxy-hemoglobin and deoxy-hemoglobin to characterize the tissue affected by a medical condition. In another embodiment, the visualization method as disclosed in the present application helps in mapping the regions of oxy-hemoglobin and deoxy-hemoglobin to characterize the tissue affected by diabetes. In most embodiment, the visualization method as disclosed in the present application helps in mapping the regions of oxy-hemoglobin and deoxy-hemoglobin to characterize the tissue affected by diabetic foot ulcers.

In one embodiment, hyperspectral matrix elements derived from the MHSI is used to visualize the biological tissue and compare the diseased biological tissue with a normal biological tissue. In another embodiment, hyperspectral matrix elements from the MHSI are scaled to displayable values to visualize the biological tissue.

In one embodiment, a scaling transformation process is used to scale the hyperspectral matrix elements to displayable values. In another embodiment, a scaling transformation process via a gamma correction factor is used to scale the hyperspectral matrix element to displayable values. In most embodiments, a scaling transformation process via a linear mapping is used to scale the hyperspectral matrix elements to displayable values.

In one embodiment, the linear mapping function applies a linear transformation to its elements for a MHSI matrix. In another embodiment, the linear mapping function applies a linear transformation to the elements of MHIS matrix.

In one embodiment, a process to convert MHSI to RGB image is disclosed. In another embodiment, a process to convert MHSI to RGB image is disclosed.

In one embodiment, the process comprise of collecting the MHSI of high-spectral resolution of the biological tissue from a patient suffering from a medical condition; predicting the three HS bands of the visible spectrum; calculating the displayed luminance for each pixel value by performing a scaling transformation via a gamma correction factor to all the three selected bands and producing a sub-spectral color image by using XYZ to RGB matrix transformation as disclosed. In another embodiment, the process comprise of collecting the MHSI of high-spectral resolution of the biological tissue from a patient suffering from a medical condition; predicting the three HS bands of the visible spectrum; calculating the displayed luminance for each pixel value by performing a scaling transformation via a linear mapping to all the three selected bands and producing a sub-spectral color image by using XYZ to RGB matrix transformation as disclosed.

In one embodiment, the process as disclosed comprise of collecting the MHSI of high-spectral resolution of the biological tissue from a patient suffering from a medical condition; predicting a red, a green and a blue band from the visible spectrum; calculating the displayed luminance for each pixel value by applying the gamma correction factor to red, blue and green bands and producing a matrix; producing a sub-spectral color image by using XYG to RGB matrix transformation as disclosed. In another embodiment, the process as disclosed comprise of collecting the MHSI of high-spectral resolution of the biological tissue from a patient suffering from a medical condition; predicting a red, a green and a blue band of the visible spectrum; calculating the displayed luminance for each pixel value by applying the linear mapping to red, blue and green bands and producing a matrix; producing a sub-spectral color image by using XYZ to RGB matrix transformation as disclosed.

In one embodiment, a XYZ to RGB transformation equation as disclosed is used to convert MHIS to RGB images.

In one embodiment, the process comprise of collecting the MHSI of high-spectral resolution of the affected tissue from a patient suffering from a medical condition; predicting a red, a green and a blue band of the visible spectrum; calculating the displayed luminance for each pixel value by applying the gamma correction factor or by applying the linear mapping to red, blue and green bands and producing a matrix sub-spectral color image by using the XYZ to RGB matrix transformation as disclosed.

In one embodiment, a method of diagnosing a biological tissue abnormality is disclosed comprising of selecting the biological tissue or area of biological tissue to be diagnosed; collecting information for vital signs and other parameters relevant to a particular medical condition; generating a MHSI; converting the MHSI to RGB image; and identifying areas of biological tissue that are at a risk for a medical condition. In another embodiment, a method of diagnosing the onset or severity of diabetic foot ulcers is disclosed comprising of selecting the area of the foot with signs of ulcers or damage; collecting vital parameters information; exposing the foot area to the imaging device; generating the MHSI and converting the MHSI to RGB image with the disclosed algorithm. In most embodiments, a method of diagnosing the severity of ulcers and further designing the treatment therapy is disclosed.

Embodiments of the invention as disclosed helps in visualization of MHSI through the disclosed algorithm by converting the MHSI to RGB images. In another aspect, the embodiments of the disclosed invention further helps in comparison studies of normal biological tissue with a diseased biological tissue to ascertain the medical condition.

Other features will be apparent from the accompanying figures and from the detailed description that follows.

BRIEF DESCRIPTION OF THE DRAWINGS

Example embodiments are illustrated by way of example and no limitation in the tables and in the accompanying figures, like references indicate similar elements and in which.

Other features of the present embodiments will be apparent from the accompanying figures and from the detailed description that follows.

DETAILED DESCRIPTION

Unless defined otherwise, all technical and scientific terms used herein have the same meaning as commonly understood by those of ordinary skill in the art to which the invention belongs.

The term 'gamma correction factor' as used herein is one of the non-linear operation which is used to code and decode luminance in videos and still image system. It helps in maximizing the use of the bits or bandwidth relative to how humans perceive light and color (3) and thus components for properties of human vision.

The term 'vital signs' as used herein corresponds to measures of different physiological statistics of a patients/person to assess the basic body functions such as body temperature, pulse rate, heart rate, blood pressure, respiratory rate and other basic parameters depending on the medical condition.

The term 'linear mapping' as used herein is a function between 2 modules that preserves the operations of module addition and scalar multiplication.

The term 'RGB image' as used herein is a color model comprising of components of Red, Green and Blue (RGB) light from the visible region of electromagnetic spectrum.

The resulting image as produced is a combination of the three primary RGB colors with different degrees of lightness (4).

The term 'scaling transformation' as used herein is a transformation which scales the coordinates of an object. It is specified either by working directly with the local coordinates or by expressing the coordinates in terms of frames (5).

The term 'medical condition' is used in its scientifically accepted sense to refer a disease condition as compared to a normal condition. The 'medical condition' as used herein may include Cancer, Tumors, Diabetes Foot Ulcers, Ulcers, Skin diseases, Neurological diseases, Vascular diseases, Muscular diseases, Cardiovascular diseases among other known disease conditions.

Although the present embodiments have been described with reference to specific example embodiments, it will be evident that various modifications and changes may be made to these embodiments without departing from the broader spirit and scope of the various embodiments.

Several embodiments of the present disclosure discuss a unique algorithmic way to convert MHSI of a biological tissue to a RGB image for a better visualization.

HSI spectroscopy since its discovery finds many applications ranging from agriculture, astronomy, chemical, environment and now finds its use in medical imaging. HSI was originally defined as a spectral sensing technique which acquires hundreds of contiguous narrow waveband images in the visible and IR regions of electromagnetic spectrum (6). The use of the technique has further extended into physiology and pathology areas of medicine to understand changes in living tissues in animal and human studies and thus is known as MHSI. As HSI depicts changes in material composition or gives information on different material present in the environment similarly MHSI gives information on chemical composition of biological tissues. The primarily absorbers are oxy- and deoxy-hemoglobin and thus MHSI characterize the in-vivo absorption spectra of these compounds in biological tissue by differentiating between the light absorbed and reflected by oxy-hemoglobin and deoxy-hemoglobin. The technology provides very important information regarding different physiological parameters such as oxygen delivery, oxygen extraction, total hemoglobin and water with spatial patterns at the level of microcirculation. Thus, the spectral and spatial features of MHSI can be combined to differentiate between two different states of biological tissue usually a normal tissue and a diseased tissue. However, the complexity of the results and the cost associated with MHSI as a whole is a disadvantage to the analytical technique. However, transforming the images from MHSI to RGB images will help in evaluating the complex MHSI into a more user friendly, easily evaluated RGB images. Further, it will help in making clinical decisions by monitoring the diseased and normal tissue and designing the mode of therapy.

Various embodiments of the invention discuss the use of disclosed algorithm to convert MHSI to RGB images which are user friendly, monitor and computer friendly, less complicated and more informative for predicting oxygen levels in a biological tissue of patients with medical conditions.

Figure 1:
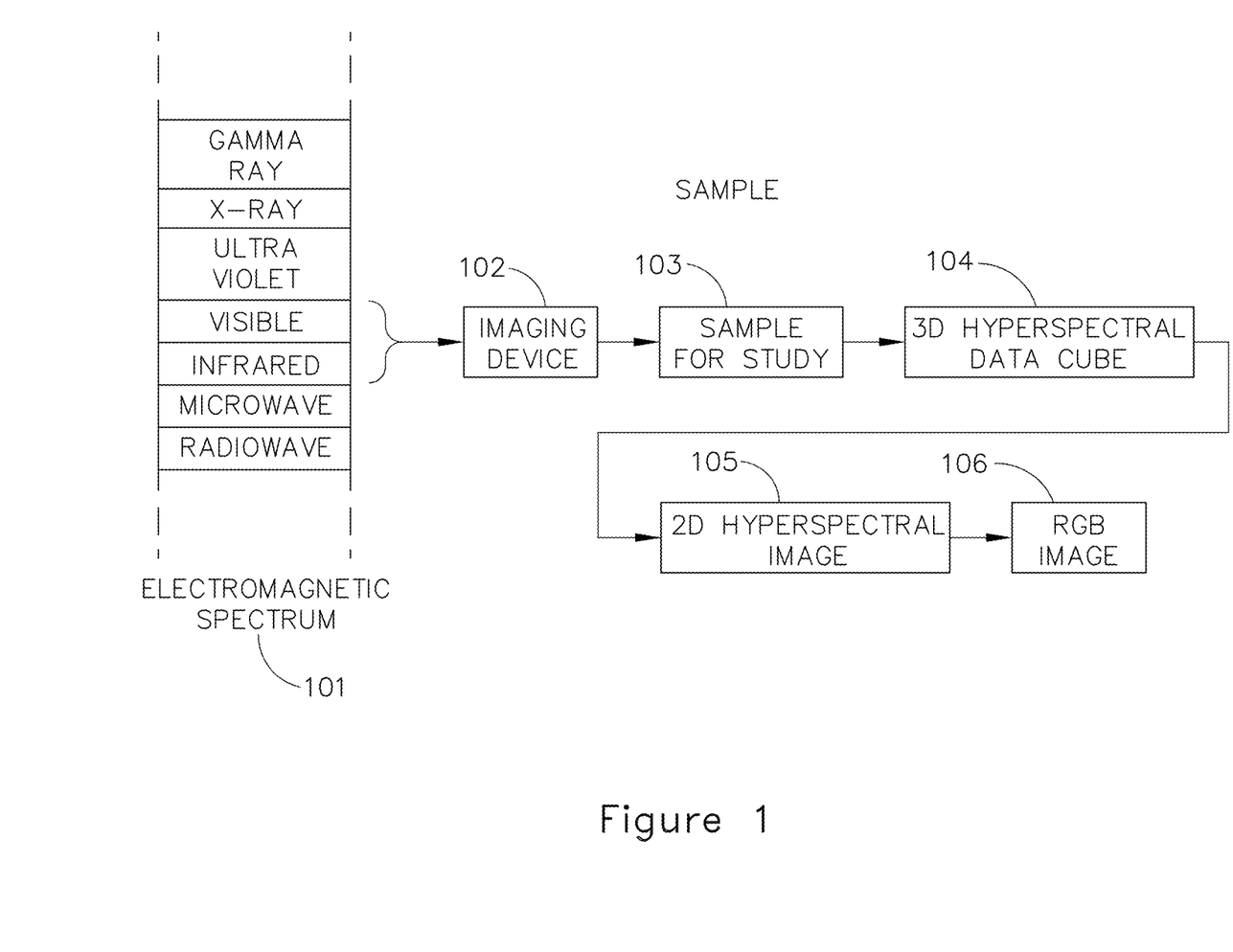
FIG. 1 shows the MHSI formation and converting MHSI to RGB image.

FIG. 1 shows the formation of MHSI and further conversion of MHSI to RGB images. Hyperspectral imaging device 102 works in the visible and infrared (IR) regions of the electro magnetic (EM) spectrum 101 and thus are able to produce 2D MHSI 105. MHSI is a collection or a set of different images each corresponding to a particular wavelength band. It is based on the concept that each pixel from the biological tissue under investigation contains detailed information about the spectrum of the incoming light. It acquires the image in cubes of data comprising rich information regarding the biological tissue in the image. Thus the pixels collected from the sample is in the form of a 3-D hyperspectral data cube 103 which is then converted into 2D MHSI 104. 2D MHSI are in a mix of colors which result in increase in its complexity for analysis and may result in poor analysis of the image obtained especially in case of human tissue analysis may affect the treatment decisions. Thus, to make the MHSI more user friendly and to simplify the image for a better interpretation, is converted into RGB image 105 with the help of disclosed algorithm. The developed algorithm utilizes the MHSI spectrum to determine accurate oxygenation level, with an error of less than 0.2%.

Figure 2:
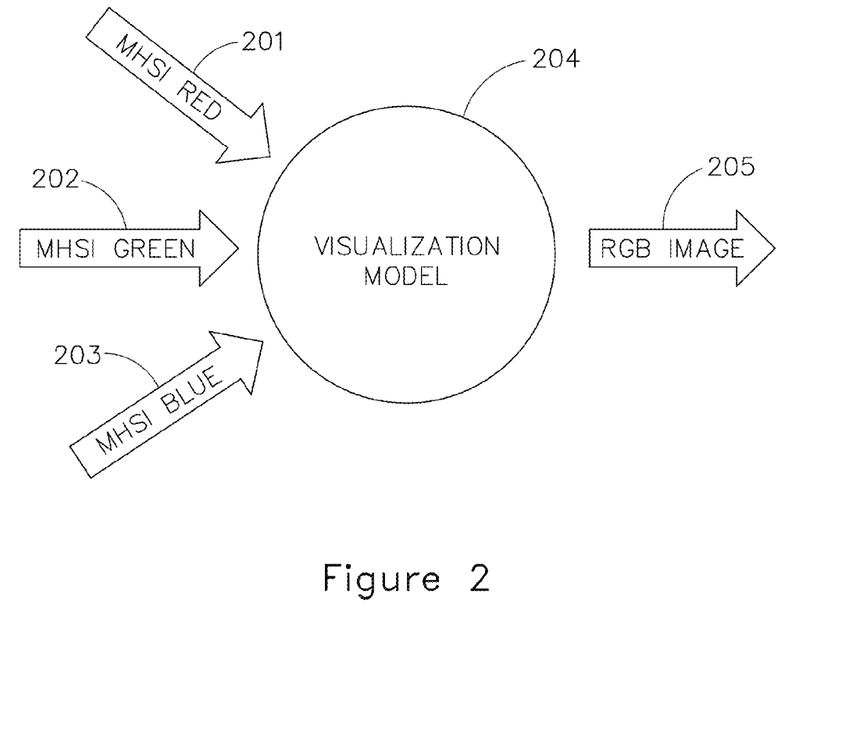
FIG. 2 shows a visualization model for MHSI to RGB image transformation.

FIG. 2 shows the visualization model to convert MHSI into RGB images. A particular wavelength (λ) from all the three bands such as red (i,j, 201), green (i,j, 202) and blue (i,j, 203) is selected which is from the visible spectrum of the image. The values are then processed in the visualization model 204 to convert the MHSI to a RGB image 205. To convert the images for visualization, the RGB matrix produced from MHSI (RGB i,j) is subjected to an algorithm as disclosed in the present application. The visualization model 204 as shown is FIG. 2 comprise of predicting the luminance for each pixel value as selected and applying either the gamma correction factor to the 3 hyper spectral bands RGB (i,j) or by applying linear mapping to the 3 hyperspectral bands RGB (i,j) to produce 1 single color image depicting red, green and blue components of the visible spectrum.

To produce RGB image from MHSI, a scaling transformation via linear mapping is used to scale the HS matrix elements to displayable values. For any MHSI matrix, M, the linear mapping function applies a linear transformation to its elements, with the lower value mapping to 0.0 and the highest value mapping to 1.0 to 2.0. The linear transformation as disclosed in the present application is given by the equation:

$$M_{lmap}(i, j) = \frac{M(i, j) - M_{min}}{M_{max} - M_{min}} \qquad \text{Equation 1}$$

Following, a sub-spectral resolution of color images is produce from MHSI by using the XYZ to RGB matrix [RGB (i,j)] transform as disclosed:

$$sRGB(i,j) = XYZ\_sRGB(M_{lmap}(i,j,\lambda)) \qquad \text{Equation 2}$$

Figure 3:
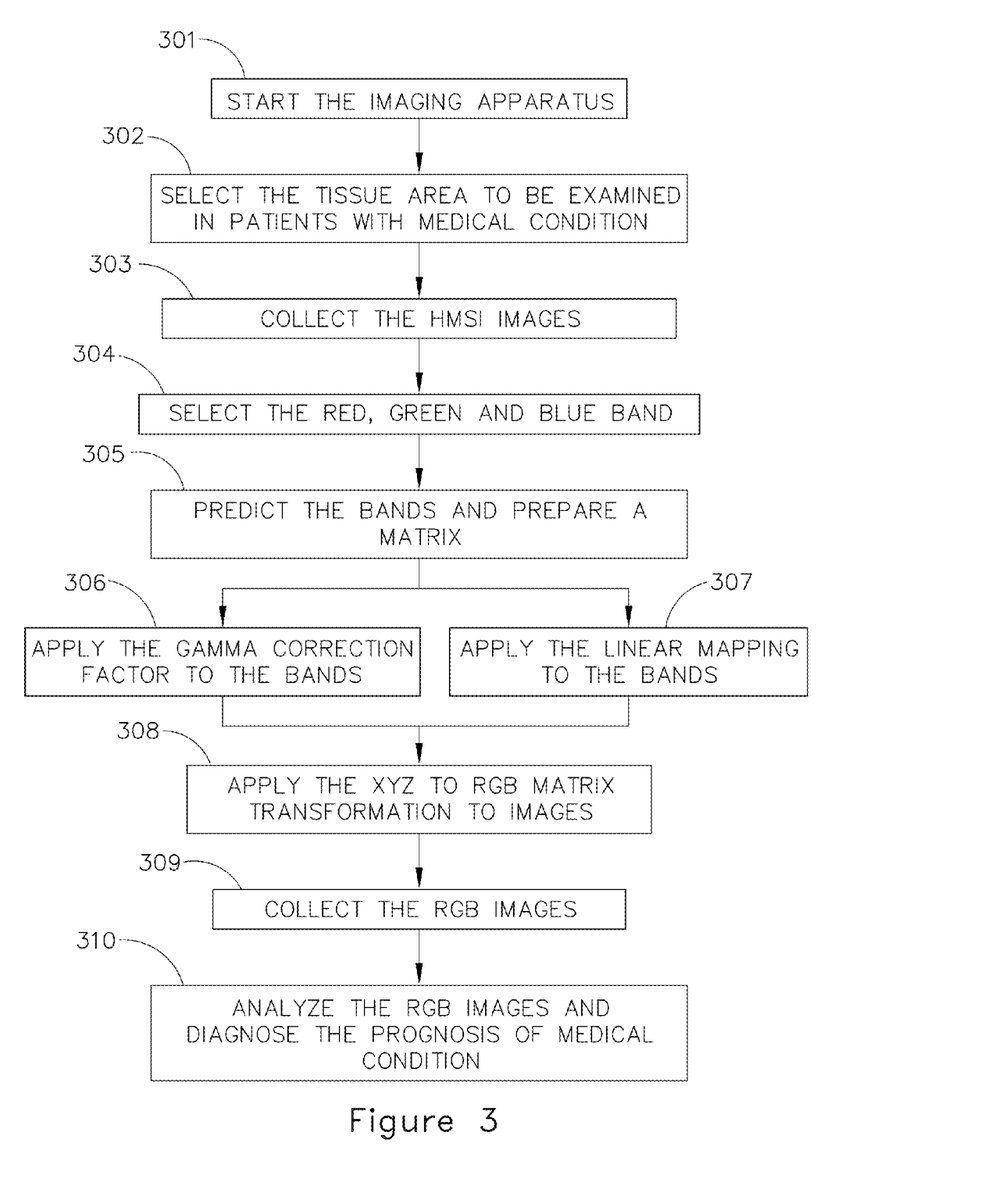
FIG. 3 shows a flow-chart representation of steps for converting MHSI into RGB images.
Figure 4A:
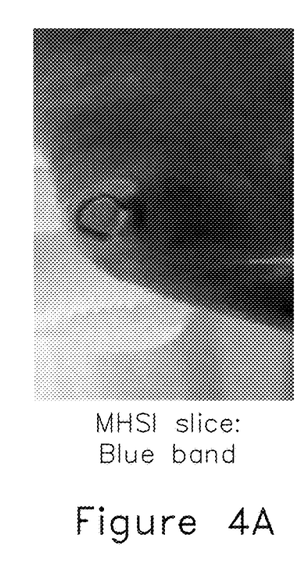
FIG. 4a, 4b, 4c, 4d shows the three MHSI slices of Blue (4a), Green (4b) and Red (4c) bands respectively selected from MHSI cube of images and the output image (4d) produced.
Figure 4B:
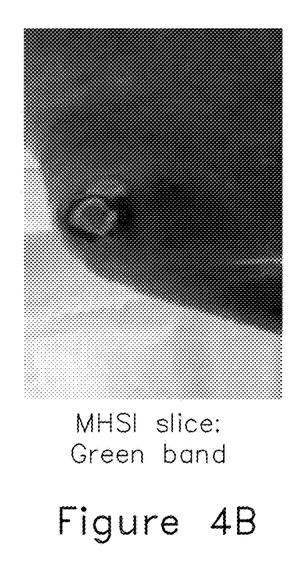
Figure 4C:
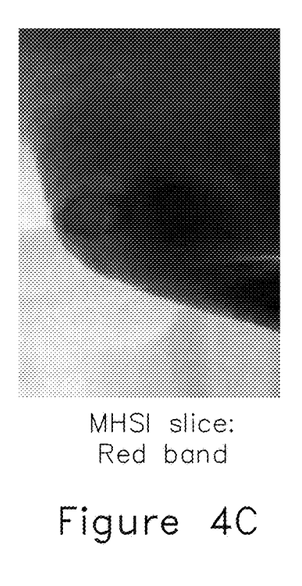
Figure 4D:
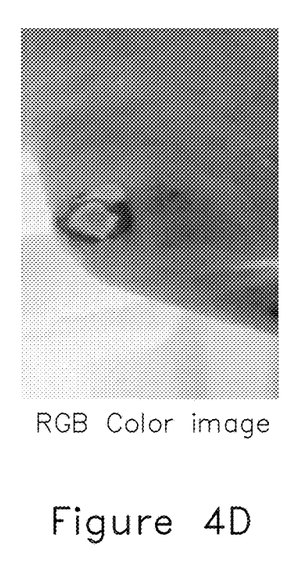

FIG. 3 shows the steps involved to carry out the disclosed invention. For this, a user or a trained technician may start the imaging apparatus 301 which may be any hyperspectral imaging apparatus available commercially or non-commercially. A user may then select the biological tissue area to be investigated in patients with a medical condition 302. The area of a biological tissue to be investigated is then exposed to the imaging device to collect the MHSI 303. From the 2D MHSI (303) select the Red, Green and Blue bands 304 and predict the matrix for each band as Red (i,j), Green (i,j) and Blue (i,j) respectively 305. Calculate the luminance to be displayed for each pixel value from the MHSI coordinates by either applying the gamma correction factor 306 or by applying the linear mapping to the band matrix 307. The values so obtained are put into the disclosed algorithm of XYZ to RGB matrix transformation 308 to produce a sub-spectral resolution of color images. Collect the RGB images converted from the MHSI 309. A user/physician may then analyze the RGB image 310 to determine the accurate oxygenation and de-oxygenation saturation levels in the biological tissue under investigation. The information may then help in analyzing the condition of the tissue, extent of tissue damage, onset of ulcers or tumors, degree of tumor or ulcers growth. A user may also extract information such as oxygen delivery, oxygen extraction, total hemoglobin, water among other information. The information obtained can then be combined with vital signs, pressure readings and other relevant information to get a clear and general picture of patient's medical condition.

FIGS. 4a, 4b, 4c and 4d show the use of disclosed algorithm to convert the MHSI images produced from the known technology of University of Nottingham to RGB image in condition of foot ulcers in patients with diabetes. The figure shows different slices from MHSI corresponding to 3 different bands of visible region. Blue (4a), Green (4b) and Red (4c) bands are selected from the 3D-MHSI and the disclosed transformation algorithm (equation 2) is applied to the band matrix to derive a RGB image (4d). The image (4d) as shown in FIG. 4 helps in predicting the saturation levels of oxygenation and de-oxygenation as they can differentiate the levels with simple color contrast rather than complex color analysis.

Figure 5A:
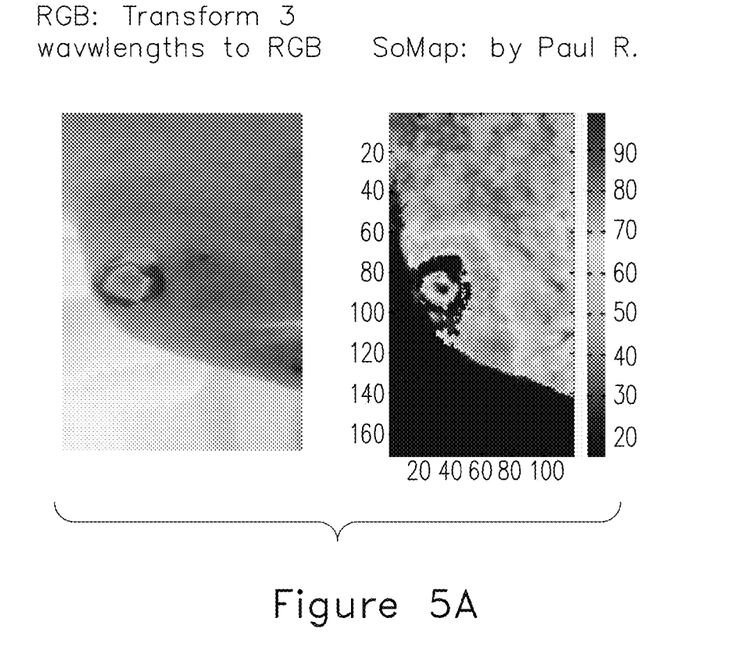
FIGS. 5A and 5B shows the comparison study between MHSI and RGB images in plantar and dorsum regions of the foot of a patient with diabetic foot ulcers respectively.
Figure 5B:
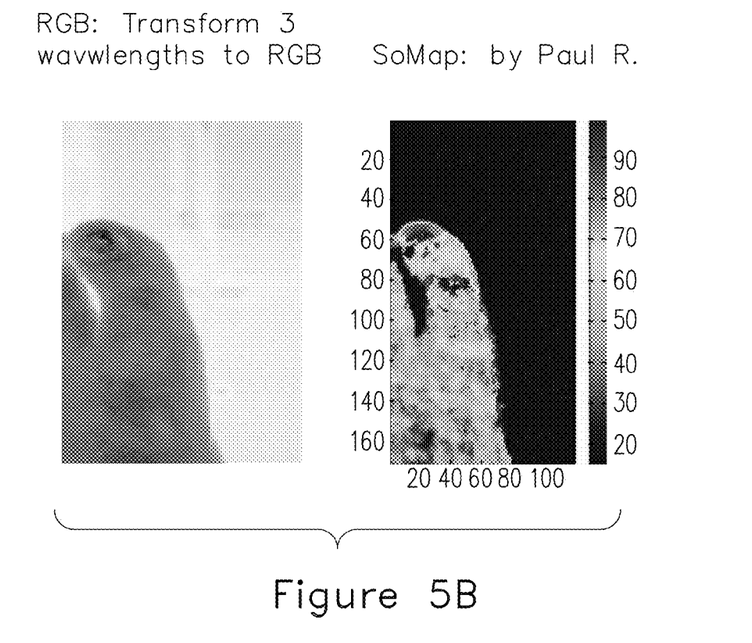

FIGS. 5a and 5b shows the comparison studies of RGB images and MHSI of foot ulcers from patients with diabetes. Ulcers in plantar (5a) and dorsum (5b) regions of the foot of the diabetic patient are being investigated. The figure demonstrate HSI produced by University of Nottingham using algorithm developed by them through Matlab using Mathworks® and RGB images produced by inventors using the disclosed algorithm. The images can determine the accurate oxygenation and de-oxygenation levels in the plantar and dorsum regions of the foot ulcers in patients with diabetes with easy visualization.

While the present disclosure has been described with reference to an exemplary embodiment, changes may be made within the purview of the appended claims, without departing from the scope and spirit of the present disclosure in its aspects. Also, although the present disclosure has been described herein with reference to particular materials and embodiments, the present disclosure is not intended to be limited to the particulars disclosed herein; rather, the present disclosure extends to all functionally equivalent structures, methods and uses, such as are within the scope of the instant claims. Accordingly, the specification and drawings are to be regarded in an illustrative rather than in a restrictive sense.

What is claimed is:

1. A method, comprising,
   selecting a biological tissue area for investigation in patients with a diabetic foot ulcer;
   scanning the biological tissue area for investigation under a medical hyperspectral imaging device;
   collecting a 2D medical hyperspectral image (MHSI) of the biological tissue area under investigation;
   converting the 2D MHSI to a color image as a red blue and green (RGB) image of the biological tissue area under investigation, wherein
   a red, green, and blue band value is selected from the visible spectrum of 2D MHSI followed by predicting a luminance matrix for each band value; calculating luminance to be displayed for each band value by applying a scaling transformation; and producing a single color image depicting red, green, and blue components of the visible spectrum wherein the 2D MHSI is converted to the RGB image by a XYZ to RGB matrix transformation using:

$$sRGB(i,j)=XYZ\_sRGB(M_{lmap}(i,j,\lambda));$$

and wherein the scaling transformation is via a linear mapping using a M, the linear mapping function applies the linear transformation to its elements for the $$M_{lmap}(i,j) = \frac{M(i,j) - M_{min}}{M_{max} - M_{min}}$$

wherein MHSI matrix, M, is calculated by applying linear transformation to the three bands red (i,j), green (i,j), and blue (i,j); and
   visualizing the RGB image to characterize the biological tissue under investigation.

2. The method of claim 1, wherein the scaling transformation is via a gamma correction factor.

3. The method of claim 1, wherein the biological tissue area for investigation is a diabetic foot ulcer in patients with diabetes.

4. The method of claim 1, wherein the biological tissue area for investigation is tumor.

5. The method of claim 1, wherein conversion of MHSI to RGB image helps in mapping the regions of oxy-hemoglobin and deoxy-hemoglobin to characterize the biological tissue under investigation.

6. A method, comprising,
   selecting a biological tissue area for investigation;
   collecting a 2D medical hyperspectral image (MHSI) of the biological tissue area under investigation;
   converting the 2D MHSI to a color image as a red blue and green (RGB) image of the biological tissue area under investigation, wherein
   a red, green, and blue band value is selected from the visible spectrum of 2D MHSI followed by predicting a luminance matrix for each band value; calculating luminance to be displayed for each band value by applying a scaling transformation; and producing a single color image depicting red, green, and blue components of the visible spectrum wherein the 2D MHSI is converted to the RGB image by a XYZ to RGB matrix transformation using:

$$sRGB(i,j)=XYZ\_sRGB(M_{lmap}(i,j,\lambda));$$

and wherein the scaling transformation is via a linear mapping using a M, the linear mapping function applies the linear transformation to its elements for the $$M_{lmap}(i,j) = \frac{M(i,j) - M_{min}}{M_{max} - M_{min}}$$

wherein MHSI matrix, M, is calculated by applying linear transformation to the three bands red (i,j), green (i,j), and blue (i,j); and
   visualizing the RGB image as produced.

7. A process, comprising:
   collecting a 2D medical hyperspectral image (MHSI of the biological tissue and a tumor from a patient suffering from a medical condition;
   predicting the three hyperspectral bands of the visible spectrum such that a red, green, and blue band value is selected from the visible spectrum of the 2D MHSI followed by predicting a luminance matrix for each band value;

calculating the displayed luminance for each pixel value by applying a scaling transformation to all the three selected bands; and producing a sub-spectral color image by using the scaling transformation and a XYZ to RGB matrix transformation;

producing a single red blue and green (RGB) image by depicting red, green, and blue components of the visible spectrum wherein the 2D MHSI is converted to the RGB image by the XYZ to RGB matrix transformation using:

$sRGB(i,j) = XYZ\_sRGB(M_{lmap}(i,j,\lambda))$;

and wherein the scaling transformation is via a linear mapping using a M, the linear mapping function applies the linear transformation to its elements for the:

$$M_{lmap}(i, j) = \frac{M(i, j) - M_{min}}{M_{max} - M_{min}}$$

wherein MHSI matrix, M, is calculated by applying linear transformation to the three bands red (i,j), green (i,j), and blue (i,j).

8. The process of claim 7, wherein the scaling transformation is via a gamma correction factor.

* * * * *